Figure 1:
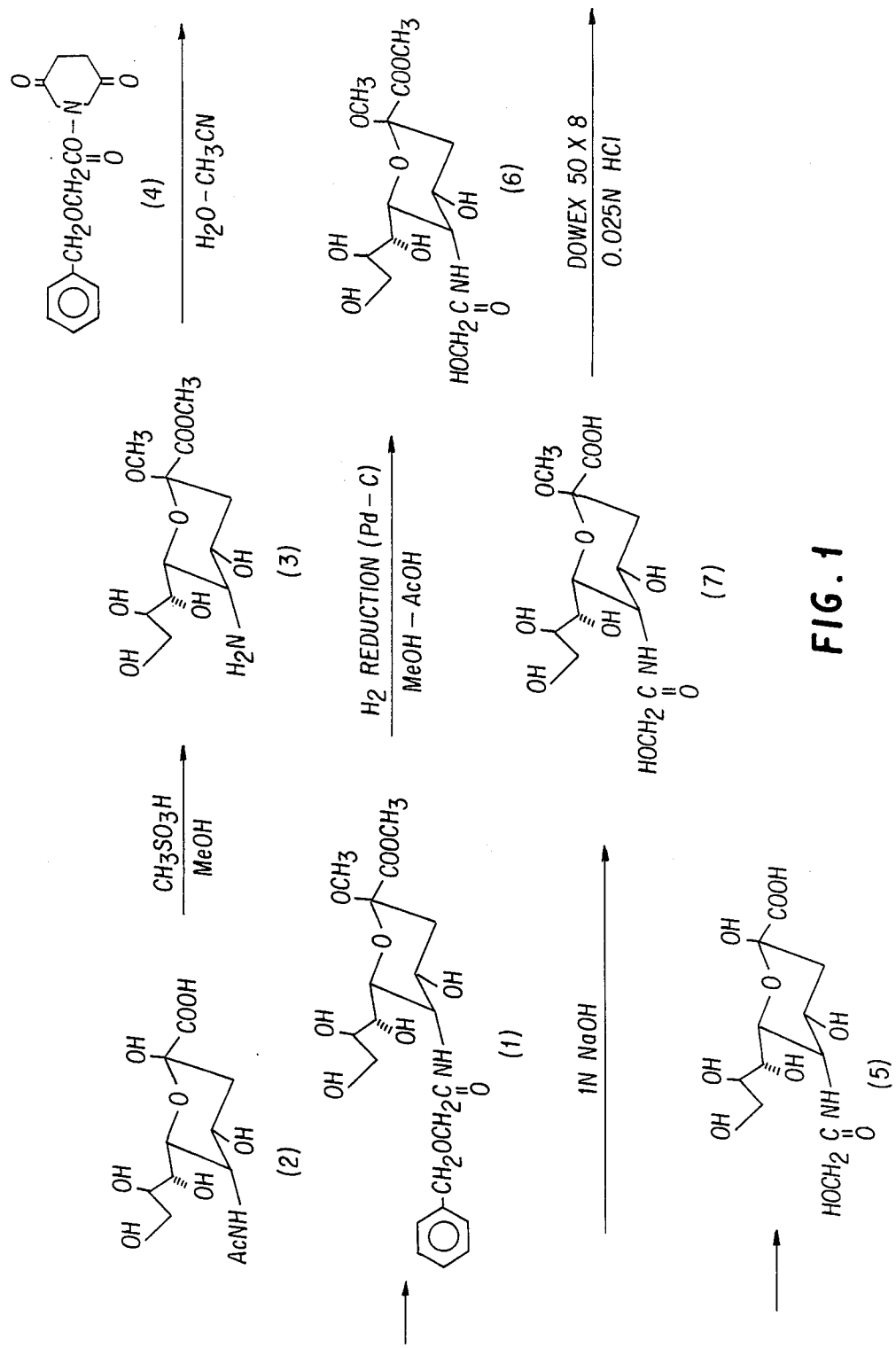

United States Patent [19]

Ogura et al.

[11] Patent Number: 4,774,327
[45] Date of Patent: Sep. 27, 1988

[54] N-GLYCOLYLNEURAMINIC ACID DERIVATIVE

[75] Inventors: Haruo Ogura, Chiba; Kimio Furuhata, Tokyo; Masayoshi Ito, Tokyo; Yoshiyasu Shitori, Tokyo, all of Japan

[73] Assignee: Mect Corporation, Tokyo, Japan

[21] Appl. No.: 917,559

[22] Filed: Oct. 10, 1986

[30] Foreign Application Priority Data

Oct. 11, 1985 [JP] Japan .................................. 60-226539

[51] Int. Cl.[4] ...................... C07H 15/04; C07H 13/04; C07B 59/00
[52] U.S. Cl. .................................... 536/18.5; 536/4.1; 536/17.2; 536/18.2; 536/18.7; 536/55.3; 536/124
[58] Field of Search ...................... 536/4.1, 18.2, 17.2, 536/18.4, 18.5, 18.7, 55.3, 53, 124

[56] References Cited

U.S. PATENT DOCUMENTS

| | | | |
|---|---|---|---|
| 4,593,091 | 6/1986 | Della Valle et al. ............... | 536/55.1 |
| 4,663,443 | 5/1987 | Shibayama et al. ............... | 536/18.2 |
| 4,675,391 | 6/1987 | Shibayama et al. ............... | 536/18.4 |
| 4,691,012 | 9/1987 | Ogura et al. ......................... | 536/55.3 |
| 4,694,076 | 9/1987 | Ogawa et al. ........................ | 536/4.1 |

FOREIGN PATENT DOCUMENTS 2101588  1/1983  United Kingdom .................. 536/53

OTHER PUBLICATIONS

Hoppe-Seyler's Z. Physiol. Chem. Bd. 350, S.111–115, Feb. 1969, "Synthesis von N-Acyl-Neuraminsauren aus Neuraminsaure-β-Methylglykosid, I".
Hoppe-Seyler's Z. Physiol. Chem. Bd. 351, S. 359–364, Mar. 1970, "N-(1-$^{14}$C)Glykoloyl-,N-Chloracetyl-und N-Fluoracetylneuraminsaure".
Biochimica et Biophysica Acta, 338(1974)369-373, "An Improved Method for the Synthesis of [14]C-Labelled or [3]H-Labelled N-Acetylneuraminic Acid".
Chemical Abstracts, vol. 72, No. 21, 25th May 1970, p. 445, Abstract No. 111774m, Columbus, OH, US; R. Schauer et al.: "Synthesis of N-Acylneuraminic Acids. II. N-[1-C] Glycoloyl-N-Chloracetyl-, and N-Fluoroacetylneuraminic Acids", & Hoppe-Seyler'S Z. Physiol. Chem 1970, 351(3), 359–64 *Abstract*.
Chemical Abstracts, vol. 64, No. 9, Apr. 25, 1966, Abstract No. 12784f, Columbus, Ohio, US; V. A. Derevitskaya et al.: "Glycopeptides XVI. Synthesis Akad. Nauk UZ. SSR 1965(4), 241–4 *Abstract*.

*Primary Examiner*—Ronald W. Griffin
*Assistant Examiner*—Nancy S. Carson
*Attorney, Agent, or Firm*—Oblon, Fisher, Spivak, McClelland & Maier

[57] ABSTRACT

This invention provides a novel compound having the following formula:

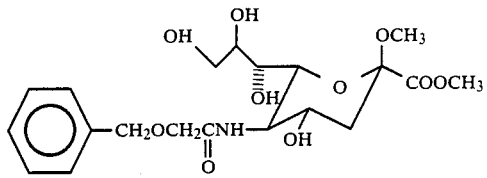

This compound is a useful intermediate for the preparation of N-glycolylneuraminic acid:

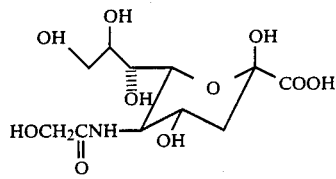

3 Claims, 1 Drawing Sheet

N-GLYCOLYLNEURAMINIC ACID DERIVATIVE

BACKGROUND OF THE INVENTION

Field of the Invention

The present invention relates to a novel N-glycolylneuraminic acid derivative, particularly to a novel compound which is a useful intermediate for the preparation of N-glycolylneuraminic acid, a substance which has recently noted to be tumor-associated antigen determinant and as a subject of interest in embryology.

Summary of the Invention

The object of the present invention is to provide a novel compound useful as an intermediate for preparation of N-glycolylneuraminic acid.

According to the present invention, a novel compound represented by the following formula (I) is provided.

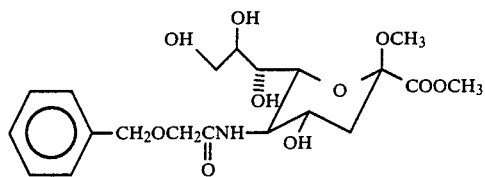

The compound of the present invention can be prepared by the following method. The preparation method is illustrated by FIG. 1.

N-acetylneuraminic acid (2) is reacted with $CH_3SO_3H$ in a solvent such as methanol at about 50° to 70° C. to produce methyl 2-O-methyl-β-D-neuraminate (3). This methyl neuraminate (3) is reacted with N-succinimidyl-O-benzylglycolate (4) in the presence of tertiary amine such as triethylamine, 4-dimethylaminopyridine, N,N-diisopropylethylamine and the like in a solvent such as water-$CH_3CN$ and the like at room temperature for about 1 to 3 hours to produce the compound (1) of the present invention.

N-acetylneuraminic acid (2) is a commercially available compound and can be obtained easily. N-succinimidyl-O-benzylglycolate (4) is a novel compound and can be prepared by reacting O-benzylglycolic acid and N,N'-succinimidylcarbonate in the presence of pyridine and the like in a solvent such as acetonitrile at room temperature.

The compound (1) of the present invention is a useful intermediate for the preparation of N-glycolylneuraminic acid (5).

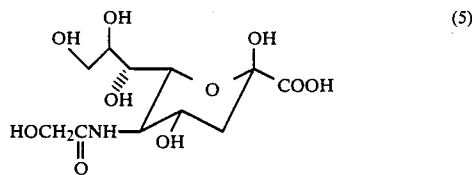

This N-glycolylneuraminic acid is a very important key compound in cancer and embryological research.

Both N-glycolyl- and N-acety-sialic acids are found in intestines, cells and humors of various animals. However, N-glycolyl-sialic acid is not present in man and domestic fowls. It is considered that this difference in the distribution of sialic acid among species of animals has some immunological significance. For example, if tissue or blood serum of other animals enters the human body, an antibody is produced to a determinant containing N-glycolylneuraminic acid, one kind of N-glycolyl-sialic acid and a serum disease type antibody (H-D antibody) is actually known as such antibody. From such immunological knowledge and the fact that the H-D antibody locates on the cancer cell surface at a high rate, N-glycolylneuraminic acid is noted to be an antigen determinant of a tumor-associated antigen.

On the other hand, Yamakawa et al, J. Biochem., 83, 1101 (1978) report a case of embryological interest relative to the difference in the distribution of N-acetyl- and N-glycolyl-sialic acids. That is, European dogs such as the Beagle and dogs from the northern part of Japan such as the Akita dog have only N-acetyl-sialic acid. However, Japanese dogs (dogs indigenous to Japan) such as the Shiba dog generally have only N-acetyl-sialic acid but some Japanese dogs having N-acetyl- and N-glycolyl-sialic acid were also found.

For example, as shown in FIG. 1, N-glycolylneuraminic acid (5), which is a compound with very interesting properties as described above, can be prepared from the compound of the present invention (1) as a raw material.

The compound (1) of the present invention is reduced in the presence of 10%Pd-C in a solvent such as MeOH—AcOH and the like at room temperature to produce compound (6). The compound (6) is treated with alkali aqueous solution to produce compound (7) and then the compound (7) is treated with Dowex 50×8 in acid solution. Whereupon N-glycolylneuraminic acid is obtained.

The present invention will now be illustrated by referring to the following nonlimitative examples.

EXAMPLE (i) Methyl β-D-2-O-methyl neuraminate (3)

0.62 g N-acetylneuraminic acid (2) was added with 50 ml methanol and 2.0 g $CH_3SO_3H$ and stirred at 60° C. for 24 hours. Then the reaction mixture is neutralized with Dowex 1×8 ($OH^-$) and the solvent was removed. The residue was dried to obtain a brown powder. The brown powder was separated and purified by column chromatography (solid phase: silica gel (Wakogel C-200), eluting solvent: ethyl acetate-ethanol) to obtain the captioned compound as a colorless powder; 0.035 g, yield: 60%).

$[\alpha]_D^{23} -53°$ (C=1, methanol).

IR $\nu_{max}^{KBr} cm^{-1}$ 3300, 1740.

Elemental analysis $C_{11}H_{21}NO_8$: Calculation: C: 44.74, H: 7.17, N: 4.74; Found: C: 44.68, H: 7.23, N: 4.54.

(ii) Methyl β-D-2-O-methyl-N-(O-benzylglycolyl)neuraminate

Compound (3) in 1 liter water was added with 1.2 g compound (4) in 40 ml acetonitrile and 0.8 g triethylamine and stirred for 2 hours. After concentration and drying of the reaction mixture, the resulting residue was separated and purified by column chromatography (solid phase: Wakogel C-300, eluting solvent: ethyl acetate-ethanol) and crystallized from ethyl acetate. The resulting crystal was recrystallized from the mixture of ethyl acetate and ethanol to obtain the captioned compound as colorless needles (1.6 g, yield: 90%).

Melting point: 182°–183° C.

$[\alpha]_D^{23} -29°$ C. (C=1, methanol).

Elemental analysis C$_{20}$H$_{29}$O$_{10}$N: Calculation: C: 54.17, H: 6.59, N: 3.16; Found: C: 53.93, H: 6.61, N: 3.14.
IR $\nu_{max}^{KBr}$cm$^{-1}$ 1745, 1665, 1550.

$^1$H-NMR (90 MHz, in d5-pyridine, δ$_H$ TMS); 2.23 (1H, dd, J=12 and 13 Hz, 3-Hox); 2.88 (1H, dd, J=4.5 and 12 Hz, 3-Heq); 3.58 (3H, s, COOMe), 3.64 (3H, s, OMe); 4.12 (2H, s, —COCH$_2$O—), 4.51 (2H, s,

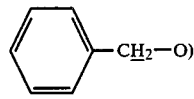
)

7.30 (5H, s,

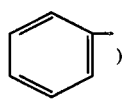
)

8.55 (1H, d, J=7 Hz, NH).

REFERENCE EXAMPLE 1

Preparation of N-glycolylneuraminic acid 1 g compound (1) was dissolved in a mixture of 10 ml methanol and 2 ml acetic acid and added with 500 mg 10%Pd-C, followed by shaking in a hydrogen stream at room temperature for 3 hours. Then, the reaction mixture was filtered and the solvent was removed from the resulting filtrate to obtain a colorless powder. The powder was recrystallized from ethanol to obtain compound (6) as colorless needles (0.70 g, yield: 88%).

Compound (6) was dissolved in 1N NaOH 10 ml and allowed to stand at room temperature for 12 hours. Then the reaction mixture was neutralized with Dowex 50×8 (H$^+$), evaporated to dryness to obtain an oil. The oil was crystallized and recrystallized from acetic acid and water to obtain a colorless prismatic N-glycolylneuraminic acid (5) (0.36 g, yield: 40%).

(compound (6))

Melting point: 203°–204° C.
[α]$_D^{23}$ −39° (C=1, methanol).
Elemental analysis C$_{13}$H$_{23}$O$_{10}$N: Calculation: C: 44.19, H: 6.56, N: 3.96; Found: C: 44.07, H: 6.53, N: 3.86.
IR $\nu_{max}^{KBr}$cm$^{-1}$ 1744, 1645, 1545.

(compound (5): N-glycolyl neuraminic acid)

Melting point: 184°–185° C. (decomposition).
[α]$_D^{23}$ −32° (C=1, H$_2$O).
Elemental analysis C$_{11}$H$_{19}$O$_{10}$N: Calculation: C: 40.62, H: 5.89, N: 4.31; Found: C: 40.71, H: 5.90, N: 4.28.

REFERENCE EXAMPLE 2

Preparation of N-succinimidyl-O-benzylglycolate (4)

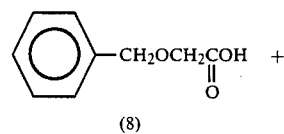
(8)

-continued

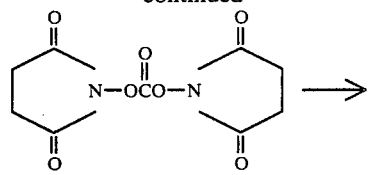
(9)

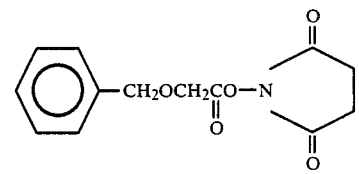
(4)

2.1 g O-benzylglycolic acid (8) was dissolved in 50 ml acetonitrile and added with 3.9 g N,N'-disuccinimidylcarbonate (DSC) (9) and 1.2 g pyridine, followed by agitation at room temperature for 6 hours. After the completion of the reaction, the solvent was removed and the residue was added with 50 ml ethyl acetate and washed successively with 5%NaHCO$_3$, saturated brine, 1N HCl and saturated brine. The resulting mixture was dried with sodium nitrate and the solvent was removed. The resulting oil was recrystallized from a mixture of ether and ethyl acetate to obtain compound (4) as colorless needles (3.0 g, yield: 85%).

Melting point: 75°–77° C.
IR $\nu_{max}^{KBr}$cm$^{-1}$ 1820, 1782, 1730.
Elemental analysis C$_{13}$H$_{13}$NO$_5$: Calculation: C: 59.31, H: 4.98, N: 5.32; Found: C: 59.28, H: 5.00, N: 5.24.

We claim:
1. A compound represented by the formula (1)

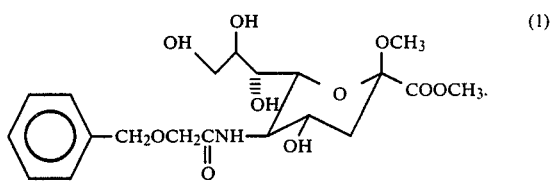

2. A process of preparing a compound represented by the formula (1):

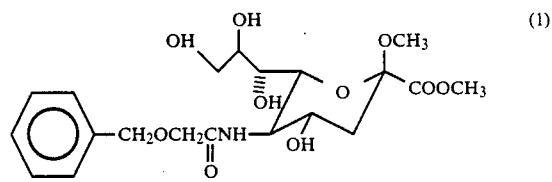

which comprises reacting a compound represented by the formula (3):

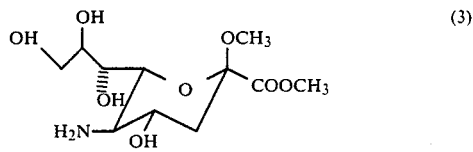

with a compound represented by the formula (4):
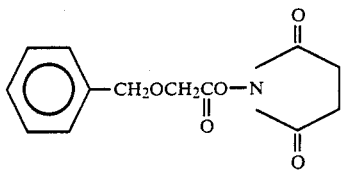
in the presence of tertiary amine, wherein the tertiary amine is at least one compound selected from the group consisting of triethylamine, 4-dimethylaminopyridine and N,N-diisopropylethylamine; and a solvent for from 1 to 3 hours.
3. The process of claim 2 wherein the solvent is a mixture of water and acetonitrile.
* * * * *